(12) United States Patent
Nozawa et al.

(10) Patent No.: US 7,632,965 B2
(45) Date of Patent: Dec. 15, 2009

(54) METHOD FOR PRODUCING (METH)ACRYLATE DERIVATIVE HAVING ISOCYANATE GROUP

(75) Inventors: Kaneo Nozawa, Fukushima (JP); Katsutoshi Morinaka, Fukushima (JP)

(73) Assignee: Showa Denko K.K., Tokyo (JP)

( * ) Notice: Subject to any disclaimer, the term of this patent is extended or adjusted under 35 U.S.C. 154(b) by 260 days.

(21) Appl. No.: 10/594,231

(22) PCT Filed: Mar. 22, 2005

(86) PCT No.: PCT/JP2005/005655

§ 371 (c)(1),
(2), (4) Date: Sep. 25, 2006

(87) PCT Pub. No.: WO2005/092842

PCT Pub. Date: Oct. 6, 2005

(65) Prior Publication Data

US 2007/0197762 A1    Aug. 23, 2007

Related U.S. Application Data

(60) Provisional application No. 60/558,550, filed on Apr. 2, 2004, provisional application No. 60/632,949, filed on Dec. 6, 2004.

(30) Foreign Application Priority Data

Mar. 25, 2004 (JP) ............................ 2004-089363
Nov. 25, 2004 (JP) ............................ 2004-339776
Jan. 31, 2005 (JP) ............................ 2005-023176

(51) Int. Cl.
*C07C 263/20* (2006.01)
*C07C 265/04* (2006.01)

(52) U.S. Cl. ...................................................... 560/213
(58) Field of Classification Search ....................... None
See application file for complete search history.

(56) References Cited

U.S. PATENT DOCUMENTS 2,821,544 A     1/1958  Holtschmidt
6,222,066 B1 *  4/2001  Danielmeier et al. ......... 560/352
6,245,935 B1 *  6/2001  Misu et al. ................... 560/218

FOREIGN PATENT DOCUMENTS

EP    0 936 214 A2    8/1999
EP    1 046 636 A2   10/2000

OTHER PUBLICATIONS

Polymer Journal, vol. 22, No. 8, pp. 689-695 (1990).
Korean Office Action dated Aug. 29, 2007.

* cited by examiner

*Primary Examiner*—Daniel M Sullivan
*Assistant Examiner*—Yevegeny Valenrod
(74) *Attorney, Agent, or Firm*—Sughrue Mion, PLLC

(57) ABSTRACT

The invention aims to provide a method whereby (meth) acrylate derivatives having an isocyanate group can be obtained in high yield by dehydrochlorination of 3-chloropropionate derivatives having an isocyanate group under industrially advantageous and mild conditions, and the content of residual hydrolyzable chlorine can be reduced. A method for producing a (meth)acrylate derivative having an isocyanate group comprises performing dehydrochlorination of a 3-chloropropionate derivative having an isocyanate group in the presence of a basic nitrogen compound having a tertiary nitrogen, the tertiary nitrogen of the basic nitrogen compound having at least one group other than an aromatic ring group.

10 Claims, No Drawings

METHOD FOR PRODUCING (METH)ACRYLATE DERIVATIVE HAVING ISOCYANATE GROUP

CROSS REFERENCES OF RELATED APPLICATION

This application is an application filed under 35 U.S.C §111(a) claiming benefit pursuant to 35 U.S.C §119(e) of the filing dates of Provisional Application No. 60/558,550 filed on Apr. 2, 2004 and 60/632,949 filed on Dec. 6, 2004 pursuant to 35 U.S.C §111(b).

TECHNICAL FIELD

The present invention relates to a method for producing (meth)acrylate derivatives having an isocyanate group that are useful for making various functional polymer materials.

BACKGROUND ART (Meth)acrylate derivatives having an isocyanate group are compounds useful in producing various functional polymers.

A common method for preparing the (meth)acrylate derivatives having an isocyanate group is to react a salt of (meth)acrylic acid and aminoalcohol ester, with phosgene. Alternatively, the derivatives are synthesized by reacting isopropenyloxazoline and phosgene. However, these methods have problems in that side reaction occurs which is addition reaction to the double bond of the (meth)acryloyl group, and polymerization is induced during the reaction because of the presence of double bonds, resulting in a loss.

Furthermore, dehydrochlorination of 3-chloropropionate derivatives having an isocyanate group has been proposed as a method for preparing the (meth)acrylate derivatives having an isocyanate group in U.S. Pat. No. 2,821,544 (Patent Document 1).

However, the patent document 1 describes only production of acryloyloxyethyl isocyanate by dehydrochlorination of isocyanatoethyl 3-chloropropionate with use of quinoline, a weakly basic tertiary amine. Moreover, since the acryloyloxyethyl isocyanate and quinoline have a small difference in boiling point, vacuum distillation separation is difficult for the product obtained by the method of the patent document 1. Further, the dehydrochlorination is performed at high temperatures (160° C.), and therefore addition of large quantities of polymerization inhibitor is required to suppress polymerization of the acryloylethyl isocyanate yielded. As described above, the method of the patent document 1 cannot satisfy the industrial requirements.

Furthermore, the conventional methods have problems of much residual hydrolyzable chlorine in the product. The (meth)acrylate derivatives having an isocyanate group that contain much hydrolyzable chlorine possibly bring about adverse effects when used as materials in various applications. Therefore, it has been required that the hydrolyzable chlorine content in the product is reduced.

DISCLOSURE OF INVENTION

The invention has an object of providing a method whereby (meth)acrylates having an isocyanate group can be obtained in high yield by dehydrochlorination of 3-chloropropionate derivatives having an isocyanate group under industrially advantageous and mild conditions, and the content of residual hydrolyzable chlorine can be reduced.

The present inventors earnestly studied in view of solving the above problems. As a result, it has been found that the use of a specific basic nitrogen compound in the dehydrochlorination of 3-chloropropionate having an isocyanate group can solve the above problems. The present invention has been completed based on the finding.

Namely, the present invention pertains to the following:

[1] A method for producing a (meth)acrylate derivative having an isocyanate group, the method comprising performing dehydrochlorination of a 3-chloropropionate derivative having an isocyanate group, the derivative being represented by the formula (1), in the presence of a basic nitrogen compound having a tertiary nitrogen to prepare a (meth)acrylate derivative having an isocyanate group, the derivative being represented by the formula (2), wherein the tertiary nitrogen of the basic nitrogen compound has at least one group other than an aromatic ring group:

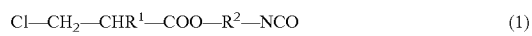

wherein $R^1$ is a hydrogen atom or a methyl group, $R^2$ is an alkylene group of 1 to 10 carbon atoms that may be branched, or a hydrocarbon group in which a cycloalkylene group of 3 to 6 carbon atoms has alkylene groups of 0 to 3 carbon atoms at ends thereof.

[2] The method for producing a (meth)acrylate derivative having an isocyanate group as described in [1], wherein the basic nitrogen compound has a boiling point lower than that of the (meth)acrylate derivative produced.

[3] The method for producing a (meth)acrylate derivative having an isocyanate group as described in [1] or [2], wherein the basic nitrogen compound is trialkylamine.

[4] The method for producing a (meth)acrylate derivative having an isocyanate group as described in [1], wherein the basic nitrogen compound is insoluble in a reaction solvent.

[5] The method for producing a (meth)acrylate derivative having an isocyanate group as described in [4], wherein the basic nitrogen compound insoluble in a reaction solvent is an ion-exchange resin having a tertiary nitrogen.

[6] The method for producing a (meth)acrylate derivative having an isocyanate group as described in any one of [1] to [5], wherein the dehydrochlorination is performed at temperatures of 40 to 120° C.

[7] The method for producing a (meth)acrylate derivative having an isocyanate group as described in any one of [1] to [6], wherein the dehydrochlorination is followed by distillation to remove the residual basic nitrogen compound.

[8] The method for producing a (meth)acrylate derivative having an isocyanate group as described in any one of [1] to [7], wherein the group $R^2$ is an alkylene group of 1 to 10 carbon atoms that may be branched.

[9] The method for producing a (meth)acrylate derivative having an isocyanate group as described in [8], wherein the group $R^2$ is $-CH_2-CH_2-$ or $-CH_2-CH_2-CH_2-$.

[10] The method for producing a (meth)acrylate derivative having an isocyanate group as described in any one of [1] to [9], wherein the dehydrochlorination is performed in the presence of the basic nitrogen compound in an equivalent amount of 0.5 to 10 moles per mole of alkali decomposable chlorine in a solution that contains the 3-chloropropionate derivative having an isocyanate group of the formula (1).

[11] The method for producing a (meth)acrylate derivative having an isocyanate group as described in any one of [1] to [10], wherein the hydrolyzable chlorine concentration in the product isolated by simple distillation is not more than 300 ppm.

[12] A (meth)acrylate derivative having an isocyanate group, which is obtained by the method described in any one of [1] to [11].

[13] The (meth)acrylate derivative having an isocyanate group as described in [12], wherein the hydrolyzable chlorine concentration is not more than 300 ppm.

[14] A method for reducing a hydrolyzable chlorine content, the method comprising treating a solution containing a (meth)acrylate derivative having an isocyanate group, the derivative being represented by the formula (2), and the hydrolyzable chlorine with a basic nitrogen compound having a tertiary nitrogen, wherein the tertiary nitrogen has at least one group other than an aromatic ring group:

$$CH_2=CR^1-COO-R^2-NCO \quad (2)$$

wherein $R^1$ is a hydrogen atom or a methyl group, $R^2$ is an alkylene group of 1 to 10 carbon atoms that may be branched, or a hydrocarbon group in which a cycloalkylene group of 3 to 6 carbon atoms has alkylene groups of 0 to 3 carbon atoms at ends thereof.

EFFECT OF THE INVENTION

According to the present invention, (meth)acrylate derivatives having an isocyanate group can be obtained in high yield by dehydrochlorination of 3-chloropropionate derivatives having an isocyanate group under industrially advantageous and mild conditions, and the content of residual hydrolyzable chlorine can be reduced.

Furthermore, the (meth)acrylate derivatives having an isocyanate group obtained by the method of the invention contain a vinyl polymerizable double bond and an isocyanate group in the molecule. Accordingly, the derivatives may be copolymerized with unsaturated compounds such as (meth) acrylates (e.g., methyl methacrylate and methyl acrylate) or styrenes to afford functional polymer materials having an isocyanate group. Moreover, introduction of an unsaturated bond by reacting the isocyanate group with a monomer, oligomer or polymer having active hydrogen such as the hydroxyl, amino or carboxyl group leads to materials that are curable by ultraviolet light, electron beams and heat.

Thus, the materials containing the derivatives of the invention are useful in various applications including resists, adhesives and films for use as electronic materials, dental materials, medical materials, coatings and adhesion.

BEST MODE FOR CARRYING OUT THE INVENTION

Hereinbelow, the method for producing a (meth)acrylate derivative having an isocyanate group according to the present invention will be described in detail. As used herein, the term "(meth)acryl" refers to acryl or methacryl, and the term "(meth)acrylo" refers to acrylo or methacrylo.

A method for producing a (meth)acrylate derivative having an isocyanate group according to the present invention performs dehydrochlorination of a 3-chloropropionate derivative having an isocyanate group of the formula (1) (hereinafter, the "compound (1)"), in the presence of a specific basic nitrogen compound:

$$Cl-CH_2-CHR^1-COO-R^2-NCO \quad (1)$$

A (meth)acrylate derivative having an isocyanate group obtainable by the method of the invention is a compound represented by the formula (2) (hereinafter, the "compound (2)"):

$$CH_2=CR^1-COO-R^2-NCO \quad (2)$$

In formulae (1) and (2), $R^1$ is a hydrogen atom or a methyl group, $R^2$ is an alkylene group of 1 to 10 carbon atoms that may be branched, or a hydrocarbon group in which a cycloalkylene group of 3 to 6 carbon atoms has alkylene groups of 0 to 3 carbon atoms at ends thereof.

The group $R^2$ is preferably an alkylene group of 1 to 10 carbon atoms that may be branched, more preferably —$CH_2$—$CH_2$— (ethylene group) or —$CH_2$—$CH_2$—$CH_2$— (propylene group), and particularly preferably —$CH_2$—$CH_2$— (ethylene group).

The compound (1) may be produced by a known method without limitation. Generally, it may be obtained by reacting a salt of 3-chloropropionic acid amino ester derivative represented by the following formula (3) (hereinafter, the "compound (3)"), which is formed between a 3-chloropropionic acid chloride derivative and an aminoalcohol hydrochloride, with dihalogenocarbonate such as phosgene:

$$Cl-CH_2-CHR^1-COO-R^2-NH_2 \cdot \text{protonic acid} \quad (3)$$

wherein $R^1$ and $R^2$ are as described in formulae (1) and (2).

The protonic acid shown in the formula (3) is not particularly limited, and is preferably hydrochloride in view of the occurrence of hydrogen chloride in later reaction.

(2-Aminoethyl) 3-chloropropionate hydrochloride of the formula (3) in which $R^1$ is hydrogen and $R^2$ is an ethylene group may be produced by reacting 3-chloropropionic acid chloride represented by the formula (4) with 2-aminoethanol hydrochloride:

$$Cl-CH_2-CH_2-COCl \quad (4)$$

The compounds (3) other than the (2-aminoethyl) 3-chloropropionate hydrochloride may be produced by methods similar to the aforementioned. The compound (3) may be obtained by adding hydrogen chloride to a salt of amino (meth)acrylate. It is preferable to use raw material compounds having no double bonds to avoid polymerization, leading to industrial advantages.

The dehydrochlorination is generally performed in the presence of a basic compound. The basic compound is typically a basic nitrogen-containing compound. The residual hydrogen atom on the nitrogen reacts with the isocyanate groups of the raw materials and the product, often resulting in lowered yield and disappearance of basicity of the nitrogen atoms.

Accordingly, the method of the present invention employs a basic nitrogen compound having tertiary nitrogen.

The term "basic nitrogen compound having tertiary nitrogen" means a basic nitrogen compound having no residual hydrogen atom on the nitrogen as described above. However, the basicity of a weakly basic nitrogen compound such as quinoline, in which the nitrogen atom forms a part of aromatic ring, is insufficient. Therefore, such a compound is unfavorable, in order to effectively carry out the dehydrochlorination. A nitrogen compound such as triphenylamine, in which all groups bonded to the nitrogen atom are aromatic ring groups, is also unfavorable. The term "aromatic ring group" includes a heterocyclic rings having conjugated system similar to the aromatic ring group, and may have substitutents on the ring.

The basic nitrogen compound having tertiary nitrogen, for use in the dehydrochlorination which is a key reaction in the method of the present invention, needs to contain the nitrogen to which at least one group, for example an alkyl group, other than the aromatic ring groups is bonded. More preferably, not more than one aromatic ring will be bonded to the tertiary nitrogen. The plural groups may be linked together to form a ring structure excluding structures such that the basicity is lowered like the quinoline.

Examples of the basic nitrogen compounds include trialkylamines, compounds in which two or three alkyl groups bonded to the nitrogen atom are linked together to form a ring structure (the ring may contain oxygen, sulfur or additional nitrogen atom), and amines in which one of the groups bonded to the nitrogen atom is an aromatic ring group (e.g. N,N-dialkylanilines and N,N-dialkylaminopyridines).

Specific examples include trimethylamine, triethylamine, tripropylamine, dimethylethylamine, dimethylisopropylamine, diethylmethylamine, dimethylbutylamine, dimethylhexylamine, diisopropylethylamine, dimethylcyclohexylamine, tetramethyldiaminomethane, dimethylbenzylamine, tetramethylethylenediamine, tetramethyl-1,4-diaminobutane, tetramethyl-1,3-diaminobutane, tetramethyl-1,6-diaminohexane, pentamethyldiethylenetriamine, 1-methylpiperidine, 1-ethylpiperidine, N,N-dimethylpiperadine, N-methylmorpholine, 1,8-diazabicyclo[5.4.0]-7-undecene (DBU), 1,5-diazabicyclo[4.3.0]-5-noene (DBN), 2,4-diazabicyclo[2.2.2]octane (DABCO), N,N-dimethylaniline, N,N-diethylaniline, and ion-exchange resins having tertiary nitrogen.

Of these, trimethylamine, triethylamine, tripropylamine and tetramethylethylenediamine are preferred. The basic nitrogen compounds may be used singly or in combination of two or more kinds.

In the invention, the dehydrochlorination may be carried out using the reaction liquid that has resulted from synthesis of the compound (1). It is also possible that the compound (1) synthesized as described above is purified by distillation or the like. The former case gives industrial advantages, for example fewer production steps.

The basic nitrogen compound remaining in the dehydrochlorination product that contains the compound (2) can cause polymerization of the compound (2). Therefore, the product will be preferably purified by distillation to remove the nitrogen compound.

Accordingly, for high purity separation, it is necessary that the basic nitrogen compound used in the invention has a boiling point lower than that of the (meth)acrylate derivative produced. Preferably, the product and the basic nitrogen compound differ in boiling point by 20° C. or greater, and more preferably 30° C. or greater. For example, when the product is acryloyloxyethyl isocyanate (boiling point: 200° C.), the basic nitrogen compound preferably has a boiling point of below 180° C. In the case of methacryloyloxyethyl isocyanate (boiling point: 211° C.), the basic nitrogen compound preferably has a boiling point of below 190° C.

For the basic nitrogen compound to be separated, the basic nitrogen compound may be insoluble in the solvent used in the reaction. Examples of such basic nitrogen compounds include ion-exchange resins composed of polymeric, basic nitrogen compounds.

Theoretically, the dehydrochlorination may be conducted by using a molar equivalent amount of the basic nitrogen compound per mole of the compound (1). Use of the basic nitrogen compound in excess is possible, but can result in residual basic nitrogen compound that induces polymerization depending on the conditions. On the other hand, deficient amounts of the basic nitrogen compound can cause the compound (1) to remain and the reaction will not complete. This case is likely to result when the reaction liquid contains much alkali decomposable chlorine derived from hydrogen chloride that has occurred during production of the isocyanate group.

Accordingly, the optimum amount of the basic nitrogen compound that achieves highest isolated yield of the objective compound (2) varies depending on the reaction conditions. Particularly, more factors will be involved when the dehydrochlorination is carried out using the reaction liquid that has resulted from synthesis of the compound (1) without isolation of the compound (1) from the liquid. Therefore, determination of the optimum amount of the basic nitrogen compound becomes difficult.

In the above case, the amount of the basic nitrogen compound is desirably determined in accordance with a measured amount of the alkali decomposable chlorine in the reaction liquid. Specifically, the basic nitrogen compound is used in an equivalent amount of 0.5 to 10 moles, preferably 0.8 to 5.0 moles, and more preferably 0.9 to 2.0 moles per mole of the alkali decomposable chlorine measured. The dehydrochlorination thus performed will provide a (meth)acrylate derivative having an isocyanate group in high isolated yield. As used herein, the term "alkali decomposable chlorine" means chlorine that can be determined under analysis conditions described later.

In the case where the dehydrochlorination is performed after the reaction liquid of the compound (1) has been purified by distillation or the like, the basic nitrogen compound may be used in an equivalent amount of 0.5 to 10 moles, preferably 0.8 to 5.0 moles, and more preferably 0.9 to 2.0 moles per mole of the compound (1).

The dehydrochlorination in the present method is performed in the presence of the above basic nitrogen compound while keeping the temperature at a certain level.

The reaction at high temperatures can result in polymerization of the compound (2). Accordingly, the reaction temperature is desirably in the range of 40 to 120° C., and preferably 40 to 100° C.

The reaction time varies depending on the reaction temperature and the basicity of the basic nitrogen compound, and is generally in the range of about 10 minutes to 40 hours, and preferably 30 minutes to 30 hours.

The reaction may employ a solvent that does not react with the isocyanate group. Exemplary solvents include aproticsolvents, for example hydrocarbons such as toluene and xylene; acetates such as ethyl acetate, propyl acetate and butyl acetate; and chlorine-based solvents such as methylene chloride. The solvent preferably has a boiling point lower than that of the product.

After the dehydrochlorination, the hydrochloride formed may be removed. Filtration is a typical method of removal. The use of the solvent in the reaction is advantageous in terms of workability and handling properties in removing the hydrochloride. When the reaction has been carried out in a solvent having low water solubility, the hydrochloride may be extracted using water. To reduce decomposition of the objective product, the extraction is preferably performed after the excessive basic nitrogen compound is neutralized.

When the residual basic nitrogen compound has been separated after the dehydrochlorination and hydrochloride removal as required, the compound (2) is isolated by distillation, crystallization, extraction or column chromatography, preferably by distillation.

There is particularly no limitation on the distillation operation and apparatus for isolating the compound (2). The apparatus equipped with rectification and reflux devices is preferable. A thin-film evaporator is also employable. The distillation is preferably performed at low temperatures to prevent undesired thermal history, and is generally carried out at a internal temperature of 120° C. or below. During distillation, oxygen or nitrogen monoxide diluted with an inert gas may be supplied to the system for preventing polymerization of the product.

As a result of the isolation, a (meth)acrylate derivative having an isocyanate group that has a hydrolyzable chlorine content of not more than 300 ppm can be obtained in a high yield.

Also, the hydrolyzable chlorine content may be reduce by treating the (meth)acrylate derivative having an isocyanate group with the above basic nitrogen compound as required. In this case, the basic nitrogen compound may be used in an equivalent amount of 0.1 to 10 moles, preferably 0.2 to 5.0 moles, and more preferably 0.3 to 2.0 moles per mole of the hydrolyzable chlorine.

The above treatment is performed in the presence of the above basic nitrogen compound while keeping the temperature at a certain level. The treatment at high temperatures can result in polymerization of the (meth)acrylate derivative. Accordingly, the treating temperature is desirably in the range of 10 to 120° C., preferably 10 to 100° C., and more preferably 10 to 80° C.

EXAMPLES

Hereinbelow, the present invention will be described in greater detail by Examples. However, it should be construed that the invention is not limited thereto.

In Examples, the alkali decomposable chlorine and hydrolyzable chlorine were measured as follows.

(Alkali Decomposable Chlorine)

Approximately 0.5 g of a specimen was precisely weighed into a 300-ml conical flask having a stopper, and the flask was charged with 100 ml of a methanol/purified water mixture (volume ratio: 70/30). Further, 10 ml of a 30% aqueous sodium hydroxide solution was added. Thereafter, a condenser tube was fitted to the conical flask and heating was performed under reflux in 80° C. water bath for 1 hour, followed by cooling to room temperature. Subsequently, the resulting solution was transferred into 200-ml measuring flask, and the flask was charged with a purified water up to the marked line. 10 ml of the liquid was precisely weighed into a 200-ml beaker, followed by addition of 100 ml of purified water and 1 ml of (1+1)nitric acid. Thereafter, the resultant liquid was subjected to potentiometric titration using 1/50 normal silver nitrate solution to determine the concentration of the alkali decomposable chlorine. The potentiometric titration was conducted using an automatic titrator (COM-550 manufactured by HIRANUMA SANGYO Co., Ltd.).

(Hydrolyzable Chlorine)

5 g of a specimen was weighed into a 100-ml conical flask, and the flask was charged with 35 ml of methyl alcohol and 15 ml of water. Thereafter, a reflux condenser was fitted to the conical flask and heating was performed under reflux in 80° C. water bath for 30 minutes, followed by cooling to room temperature. Subsequently, the resultant solution was subjected to potentiometric titration using 1/100 normal silver nitrate solution to determine the concentration of the hydrolyzable chlorine.

Synthesis Example 1

Synthesis of 3-chloropropionic acid chloride

A four-necked flask equipped with a thermometer, a cooling tube, a gas inlet tube and a stirrer was charged with 50 g of acrylic acid and 1 g of dimethylformamide, followed by heating to 70° C. Subsequently, 100 g of phosgene was supplied over a period of 10 hours. After completion of the supply, the excessive phosgene was removed and vacuum distillation was performed (at 60° C. and 3 kPa). 5 g of the first fraction was separated, and 3-chloropropionic acid chloride as main fraction was obtained in an amount of 50 g (80% yield).

Synthesis Example 2

Synthesis of (2-isocyanatoethyl) 3-chloropropionate

A four-necked flask equipped with a thermometer, a cooling tube, a gas inlet tube and a stirrer was charged with 250 ml of toluene and 25 g (0.41 mol) of 2-aminoethanol, followed by heating to 90° C. Subsequently, approximately 20 g of hydrogen chloride gas was supplied. Thereafter, 59 g (0.46 mol) of 3-chloropropionic acid chloride obtained in Synthesis Example 1 was added dropwise over a period of 90 minutes, and heating was performed at 90° C. for 1 hour. Further, 80 g (0.81 mol) of phosgene was supplied over a period of 4 hours. Subsequently, the dissolved phosgene and toluene were removed and distillation was performed (at 105-110° C. and 0.7 kPa). Thus, (2-isocyanatoethyl) 3-chloropropionate was obtained in an amount of 59 g (0.33 mol) (81% yield).

Synthesis Example 3

Synthesis of (2-isocyanatoethyl)3-chloro-2-methylpropionate

3-Chloro-2-methylpropionic acid chloride was synthesized by the procedure of Synthesis Example 1, except that the acrylic acid was replaced with methacrylic acid. Subsequently, (2-isocyanatoethyl) 3-chloro-2-methylpropionate was prepared by the procedure of Synthesis Example 2 except that 3-chloro-2-methylpropionic acid chloride was used.

Synthesis Example 4

Synthesis of crude (2-isocyanatoethyl)3-chloropropionate

A four-necked flask equipped with a thermometer, a cooling tube, a gas inlet tube and a stirrer was charged with 1200 ml of toluene and 131 g (2.15 mol) of 2-aminoethanol, followed by heating to 90° C. Subsequently, approximately 93 g of hydrogen chloride gas was supplied. Thereafter, 300 g (2.37 mol) of 3-chloropropionic acid chloride obtained in Synthesis Example 1 was added dropwise over a period of 90 minutes, and heating was performed at 90° C. for 1 hour. Further, 373 g (3.77 mol) of phosgene was supplied over a period of 4 hours. Subsequently, the dissolved phosgene was removed. Thus, 1100 g of a liquid was obtained that contained crude (2-isocyanatoethyl) 3-chloropropionate.

Gas chromatography analysis of the liquid resulted in 28.6% concentration of (2-isocyanatoethyl) 3-chloropropionate. That is, the above method afforded 314.6 g (1.77 mol) of (2-isocyanatoethyl) 3-chloropropionate (82% yield). Measurement of the alkali decomposable chlorine in the liquid of crude (2-isocyanatoethyl) 3-chloropropionate resulted in 8.33%.

Example 1

A three-necked flask was charged with 250 ml of toluene, 59 g of (2-isocyanatoethyl) 3-chloropropionate obtained in Synthesis Example 2, and 50 g (0.49 mol) of triethylamine (boiling point: 89.4° C.), followed by heating at 50° C. for 6 hours with stirring. After cooling to room temperature, the hydrochloride formed was filtered off. Subsequently, the excessive triethylamine and toluene were evaporated. The remainder was distilled (at 62-67° C. and 0.7 kPa) to yield 41 g (0.29 mol) of acryloyloxyethyl isocyanate (boiling point: 200° C.) (87% yield). The hydrolyzable chlorine concentration was 170 ppm.

Example 2

A three-necked flask was charged with 250 ml of toluene, 60 g (0.34 mol) of (2-isocyanatoethyl) 3-chloropropionate obtained in Synthesis Example 2, and 70 g (0.49 mol) of tripropylamine (boiling point: 156.5° C.), followed by heating at 50° C. for 6 hours with stirring. After cooling to room temperature, the hydrochloride formed was filtered off. Subsequently, the excessive tripropylamine and toluene were evaporated. The remainder was distilled (at 62-67° C. and 0.7 kPa) to yield 39 g (0.28 mol) of acryloyloxyethyl isocyanate (boiling point: 200° C.) (82% yield). The hydrolyzable chlorine concentration was 200 ppm.

Example 3

A three-necked flask was charged with 250 ml of toluene, 60 g (0.34 mol) of (2-isocyanatoethyl) 3-chloropropionate obtained in Synthesis Example 2, and 28.5 g (0.49 mol) of tetramethylethylenediamine (boiling point: 158-160° C.), followed by heating at 50° C. for 6 hours with stirring. After cooling to room temperature, the hydrochloride formed was filtered off. Subsequently, the excessive tetramethylethylenediamine and toluene were evaporated. The remainder was distilled (at 62-67° C. and 0.7 kPa) to yield 41 g (0.29 mol) of acryloyloxyethyl isocyanate (boiling point: 200° C.) (86% yield). The hydrolyzable chlorine concentration was 230 ppm.

Example 4

A three-necked flask was charged with 500 ml of toluene, 60 g (0.34 mol) of (2-isocyanatoethyl) 3-chloropropionate obtained in Synthesis Example 2, and 200 g of a dried strongly basic ion-exchange resin, followed by heating at 50° C. for 6 hours with stirring. After cooling to room temperature, the ion-exchange resin was filtered off. Subsequently, the toluene was evaporated, and the remainder was distilled (at 62-67° C. and 0.7 kPa) to yield 41 g (0.29 mol) of acryloyloxyethyl isocyanate (boiling point: 200° C.) (86% yield). The hydrolyzable chlorine concentration was 270 ppm.

Example 5

A three-necked flask was charged with 250 ml of toluene, 66 g (0.34 mol) of (2-isocyanatoethyl) 3-chloro-2-methylpropionate obtained in Synthesis Example 3, and 50 g (0.49 mol) of triethylamine (boiling point: 89.4° C.), followed by heating at 75° C. for 30 hours with stirring. After cooling to room temperature, the hydrochloride formed was filtered off. Subsequently, the excessive triethylamine and toluene were evaporated. The remainder was distilled (at 75-78° C. and 0.7 kPa) to yield 37 g (0.24 mol) of methacryloyloxyethyl isocyanate (boiling point: 211° C.) (70% yield). The hydrolyzable chlorine concentration was 220 ppm.

Example 6

A three-necked flask was charged with 250 ml of toluene, 66 g (0.34 mol) of (3-isocyanatopropyl) 3-chloropropionate obtained in Synthesis Example 2, and 50 g (0.49 mol) of triethylamine (boiling point: 89.4° C.), followed by heating at 50° C. for 6 hours with stirring. After cooling to room temperature, the hydrochloride formed was filtered off. Subsequently, the excessive triethylamine and toluene were evaporated. The remainder was distilled (at 72-75° C. and 0.7 kPa) to yield 35 g (0.23 mol) of acryloyloxypropyl isocyanate (boiling point: 230° C.) (66% yield). The hydrolyzable chlorine concentration was 250 ppm.

Comparative Example 1

A three-necked flask was charged with 250 ml of toluene, 60 g (0.34 mol) of (2-isocyanatoethyl) 3-chloropropionate obtained in Synthesis Example 2, and 63 g (0.49 mol) of quinoline (boiling point: 237.7° C.), followed by heating at 50° C. for 6 hours with stirring. No acryloyloxyethyl isocyanate was confirmed by gas chromatography analysis.

Comparative Example 2

A three-necked flask was charged with 250 ml of toluene, 60 g (0.34 mol) of (2-isocyanatoethyl) 3-chloropropionate obtained in Synthesis Example 2, and 38.8 g (0.49 mol) of pyridine (boiling point: 115-116° C.), followed by heating at 50° C. for 6 hours with stirring. No acryloyloxyethyl isocyanate was confirmed by gas chromatography analysis.

Comparative Example 3

The following procedures were carried out under the conditions described in Example 1 of U.S. Pat. No. 2,821,544. A three-necked flask was charged with 60 g (0.34 mol) of (2-isocyanatoethyl) 3-chloropropionate obtained in Synthesis Example 2 and 63 g (0.49 mol) of quinoline (boiling point: 237.7° C.), followed by heating at 160° C. for 1 hour with stirring. Gas chromatography analysis confirmed that the (2-isocyanatoethyl) 3-chloropropionate had disappeared and that acryloyloxyethyl isocyanate had formed. The reaction liquid was a viscous, blackish brown and substantially uniform liquid. Vacuum distillation of the liquid resulted in 10 g of a fraction, and a viscous liquid remained. Gas chromatography analysis of the fraction provided that the fraction obtained was a mixture of acryloyloxyethyl isocyanate and quinoline (in a ratio of about 5:4). Thus, high-purity acryloyloxyethyl isocyanate was not obtained.

Comparative Example 4

A three-necked flask was charged with 66 g (0.34 mol) of (2-isocyanatoethyl) 3-chloro-2-methylpropionate obtained in Synthesis Example 3 and 63 g (0.49 mol) of quinoline (boiling point: 237.7° C.), followed by heating at 160° C. for 1 hour with stirring. Gas chromatography analysis confirmed that the (2-isocyanatoethyl) 3-chloro-2-methylpropionate had reduced and that methacryloyloxyethyl isocyanate had formed. The reaction liquid was a viscous, blackish brown and substantially uniform liquid. Vacuum distillation of the liquid resulted in 18 g of a fraction, and a viscous liquid remained. Gas chromatography analysis of the fraction provided that the fraction obtained was a mixture of methacryloyloxyethyl isocyanate and quinoline (in a ratio of about 5:6). Thus, high-purity methacryloyloxyethyl isocyanate was not obtained.

Example 7

A 500-ml flask was charged with 111.5 g of the liquid of crude (2-isocyanatoethyl) 3-chloropropionate obtained in Synthesis Example 4, followed by addition of 0.20 g of phenothiazine and 0.20 g of 2,6-bis-t-butylhydroxytoluene. The liquid of crude (2-isocyanatoethyl) 3-chloropropionate contained 9.29 g (0.26 mol) of alkali decomposable chlorine and 31.9 g (0.18 mol) of (2-isocyanatoethyl) 3-chloropropionate. Thereafter, 26.5 g (0.26 mol) of triethylamine was added dropwise over a period of 1.5 hours. Subsequently, heating was performed at 60° C. for 8 hours with stirring, followed by cooling to room temperature. The solid formed was separated by filtration and washed with toluene.

Gas chromatography analysis of the solution obtained confirmed that 23.4 g (0.166 mol, 92.2% yield) of acryloyloxyethyl isocyanate had been obtained. The residual (2-isocyanatoethyl) 3-chloropropionate content was 2.1%.

Example 8

A 500-ml flask was charged with 111.5 g of the liquid of crude (2-isocyanatoethyl) 3-chloropropionate obtained in Synthesis Example 4, followed by addition of 0.20 g of phenothiazine and 0.20 g of 2,6-bis-t-butylhydroxytoluene. Thereafter, 25.4 g (0.25 mol) of triethylamine was added dropwise over a period of 1.5 hours. Subsequently, heating was performed at 60° C. for 8 hours with stirring, followed by cooling to room temperature. The solid formed was separated by filtration and washed with toluene.

Gas chromatography analysis of the solution obtained confirmed that 23.6 g (0.167 mol, 93.0% yield) of acryloyloxyethyl isocyanate had been obtained. The residual (2-isocyanatoethyl) 3-chloropropionate content was 5.0%.

Example 9

A 500-ml flask was charged with 111.5 g of the liquid of crude (2-isocyanatoethyl) 3-chloropropionate obtained in Synthesis Example 4, followed by addition of 0.20 g of phenothiazine and 0.20 g of 2,6-bis-t-butylhydroxytoluene. Thereafter, 39.8 g (0.39 mol) of triethylamine was added dropwise over a period of 1.5 hours. Subsequently, heating was performed at 60° C. for 8 hours with stirring, followed by cooling to room temperature. The solid formed was separated by filtration and washed with toluene.

Gas chromatography analysis of the solution obtained confirmed that 22.3 g (0.158 mol, 87.7% yield) of acryloyloxyethyl isocyanate had been obtained. The residual (2-isocyanatoethyl) 3-chloropropionate content was 0.3%.

Example 10

A 500-ml flask was charged with 111.5 g of the liquid of crude (2-isocyanatoethyl) 3-chloropropionate obtained in Synthesis Example 4, followed by addition of 0.20 g of phenothiazine and 0.20 g of 2,6-bis-t-butylhydroxytoluene. Thereafter, 63.6 g (0.62 mol) of triethylamine was added dropwise over a period of 1.5 hours. Subsequently, heating was performed at 60° C. for 8 hours with stirring, followed by cooling to room temperature. The solid formed was separated by filtration and washed with toluene.

Gas chromatography analysis of the solution obtained confirmed that 20.8 g (0.147 mol, 81.7% yield) of acryloyloxyethyl isocyanate had been obtained. The residual (2-isocyanatoethyl) 3-chloropropionate content was 0.1%.

Table 1 shows the yields and residual materials resulted in Examples 7 to 10, based on the ratio of the amounts of the basic nitrogen compound (triethylamine) relative to the alkali decomposable chlorine.

TABLE 1

| Example | Ratio* | Yield (%) | Residual Materials (%) |
|---------|--------|-----------|------------------------|
| 7 | 1.0 | 92.2 | 2.1 |
| 8 | 0.97 | 93.0 | 5.0 |
| 9 | 1.5 | 87.7 | 0.3 |
| 10 | 2.4 | 82.2 | 0.1 |

*Triethylamine (mol)/Alkali decomposable chlorine (mol)

Example 11

A three-necked flask was charged with 200 g (hydrolyzable chlorine concentration: 33000 ppm, 6.6 g, 0.19 mol) of solution containing methacryloyloxyethyl isocyanate, and 19.1 g (0.19 mol) of triethylamine, followed by heating at 40° C. for 10 hours with stirring. After cooling to room temperature, the hydrochloride formed was filtered off. Subsequently, the resulting solution was distilled (at 75-78° C. and 0.7 kPa) to yield methacryloyloxyethyl isocyanate. The hydrolyzable chlorine concentration was 1092 ppm.

Comparative Example 5

200 g (hydrolyzable chlorine concentration: 33000 ppm, 6.6 g, 0.19 mol) of solution containing methacryloyloxyethyl isocyanate was distilled (at 75-78° C. and 0.7 kPa) to yield methacryloyloxyethyl isocyanate, without treating with the basic nitrogen compound. The hydrolyzable chlorine concentration was 5262 ppm.

The invention claimed is:

1. A method for producing a (meth)acrylate derivative having an isocyanate group, the method comprising performing dehydrochlorination of a 3-chloropropionate derivative having an isocyanate group, the derivative being represented by the formula (1), in the presence of a basic nitrogen compound having a tertiary nitrogen to prepare a (meth)acrylate derivative having an isocyanate group, the derivative being represented by the formula (2), wherein the tertiary nitrogen of the basic nitrogen compound has at least one group other than an aromatic ring group:

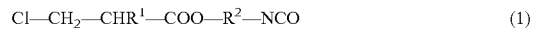

$$Cl-CH_2-CHR^1-COO-R^2-NCO \quad (1)$$

$$CH_2=CR^1-COO-R^2-NCO \quad (2)$$

wherein $R^1$ is a hydrogen atom or a methyl group, $R^2$ is an alkylene group of 1 to 10 carbon atoms that may be branched, or a hydrocarbon group in which a cycloalkylene group of 3 to 6 carbon atoms has alkylene groups of 0 to 3 carbon atoms at ends thereof, wherein the basic nitrogen compound is a trialkylamine.

2. The method for producing a (meth)acrylate derivative having an isocyanate group according to claim 1, wherein the basic nitrogen compound has a boiling point lower than that of the (meth)acrylate derivative produced.

3. The method for producing a (meth)acrylate derivative having an isocyanate group according to claim 1, wherein the basic nitrogen compound is insoluble in a reaction solvent.

4. The method for producing a (meth)acrylate derivative having an isocyanate group according to claim 3, wherein the basic nitrogen compound insoluble in a reaction solvent is an ion-exchange resin having a tertiary nitrogen.

5. The method for producing a (meth)acrylate derivative having an isocyanate group according to claim 1, wherein the dehydrochlorination is performed at temperatures of 40 to 120° C.

6. The method for producing a (meth)acrylate derivative having an isocyanate group according to claim 1, wherein the dehydrochlorination is followed by distillation to remove the residual basic nitrogen compound.

7. The method for producing a (meth)acrylate derivative having an isocyanate group according to claim 1, wherein the group $R^2$ is an alkylene group of 1 to 10 carbon atoms that may be branched.

8. The method for producing a (meth)acrylate derivative having an isocyanate group according to claim 7, wherein the group $R^2$ is —$CH_2$—$CH_2$— or —$CH_2$—$CH_2$—.

9. The method for producing a (meth)acrylate derivative having an isocyanate group according to claim 1, wherein the dehydrochlorination is performed in the presence of the basic nitrogen compound in an equivalent amount of 0.5 to 10 moles per mole of alkali decomposable chlorine in a solution that contains the 3-chloropropionate derivative having an isocyanate group of the formula (1).

10. The method for producing a (meth)acrylate derivative having an isocyanate group according to claim 1, wherein the hydrolyzable chlorine concentration in the product isolated by simple distillation is not more than 300 ppm.

* * * * *